United States Patent
Amundson et al.

(10) Patent No.: US 11,787,071 B2
(45) Date of Patent: Oct. 17, 2023

(54) DETACHABLE END EFFECTORS FOR COSMETICS ROBOTICS

(71) Applicant: Wink Robotics, Oakland, CA (US)

(72) Inventors: Kurt Amundson, Berkeley, CA (US); Mike Hughes, Oakland, CA (US); Nathan Harding, Oakland, CA (US)

(73) Assignee: WINK ROBOTICS, Oakland, CA (US)

( * ) Notice: Subject to any disclaimer, the term of this patent is extended or adjusted under 35 U.S.C. 154(b) by 288 days.

(21) Appl. No.: 17/288,282

(22) PCT Filed: Sep. 17, 2019

(86) PCT No.: PCT/US2019/051496
§ 371 (c)(1),
(2) Date: Apr. 23, 2021

(87) PCT Pub. No.: WO2020/086193
PCT Pub. Date: Apr. 30, 2020

(65) Prior Publication Data
US 2021/0387364 A1     Dec. 16, 2021

Related U.S. Application Data

(60) Provisional application No. 62/750,582, filed on Oct. 25, 2018.

(51) Int. Cl.
*B25J 15/00* (2006.01)
*B25J 19/06* (2006.01)
(Continued)

(52) U.S. Cl.
CPC ............. *B25J 19/06* (2013.01); *B25J 9/1697* (2013.01); *B25J 11/008* (2013.01); *B25J 15/0019* (2013.01)

(58) Field of Classification Search
CPC .... B25J 9/1697; B25J 15/0019; B25J 11/008; B25J 19/063; B25J 19/06; B25J 15/0441;
(Continued)

(56) References Cited

U.S. PATENT DOCUMENTS 8,113,218 B2 *  2/2012  Nguyen .................. A41G 5/02
                                                132/216
8,701,685 B2 *  4/2014  Chipman ............... A45D 44/00
                                                206/581
(Continued)

FOREIGN PATENT DOCUMENTS

DE     102005020938      11/2006
DE     202013105504       3/2015
(Continued)

OTHER PUBLICATIONS

Marvel et al., Characterizing Task-Based Human-Robot Collaboration Safety in Manufacturing, 2014, IEEE, p. 260-275 (Year: 2014).*

(Continued)

*Primary Examiner* — McDieunel Marc
(74) *Attorney, Agent, or Firm* — Everett G. Diederiks, Jr.

(57) ABSTRACT

A device for ensuring safe operation of a robot used for cosmetics applications, including the retrofitting of robots not originally design for such applications. The robot is used for the automatic placement of eyelash extensions onto the natural eyelashes of a subject. In some embodiments, a safety barrier is provided by a physical barrier or light curtain. In the invention, the robot uses an end effector which is configured to extend through the safety barrier and includes a release mechanism configured to readily release from the robot upon contacting the human subject, thereby preventing injury.

16 Claims, 11 Drawing Sheets

(51) Int. Cl.
*B25J 9/16* (2006.01)
*B25J 11/00* (2006.01)

(58) Field of Classification Search
CPC ...... B25J 9/1676; A61B 90/361; A61B 90/94; A61B 34/32; A61B 2017/00477; A61B 2090/3937; A61B 2034/2065; G05B 2219/40201; A41G 5/02
See application file for complete search history.

(56) References Cited

U.S. PATENT DOCUMENTS

| | | | |
|---|---|---|---|
| 8,752,562 B2* | 6/2014 | Dinh | A41G 5/02 132/216 |
| 8,788,093 B2 | 7/2014 | Sakakibara et al. | |
| 8,826,919 B2* | 9/2014 | Dinh | A41G 5/02 132/216 |
| 8,875,718 B2* | 11/2014 | Dinh | A41G 5/02 132/216 |
| 8,967,158 B2 | 3/2015 | Sanbonmatsu | |
| 9,451,800 B2* | 9/2016 | Dinh | A41G 5/02 |
| 9,456,646 B2* | 10/2016 | Calina | A41G 5/02 |
| 9,462,837 B2* | 10/2016 | Ngo | A41G 5/02 |
| 9,565,883 B2* | 2/2017 | Dinh | A41G 5/02 |
| 11,304,763 B2* | 4/2022 | Shelton, IV | G06F 3/017 |
| 11,423,007 B2* | 8/2022 | Shelton, IV | A61B 90/361 |
| 11,571,234 B2* | 2/2023 | Nott | A61B 17/320068 |
| 2002/0188293 A1 | 12/2002 | Manzo | |
| 2004/0078278 A1 | 4/2004 | Dauga et al. | |
| 2007/0221701 A1 | 9/2007 | Ortiz et al. | |
| 2009/0248039 A1 | 10/2009 | Cooper et al. | |
| 2011/0295242 A1 | 12/2011 | Spivey et al. | |
| 2012/0290134 A1 | 11/2012 | Zhao et al. | |
| 2016/0058513 A1 | 3/2016 | Fabio | |
| 2016/0074120 A1 | 3/2016 | Farritor et al. | |

FOREIGN PATENT DOCUMENTS

| | | |
|---|---|---|
| JP | 59-136292 | 9/1984 |
| JP | 59-163291 | 9/1984 |
| JP | 07-194610 | 8/1995 |
| JP | 2003093403 | 4/2003 |
| JP | 2016-182648 | 10/2016 |
| KR | 20150008290 | 1/2015 |
| WO | 2018/093967 | 5/2018 |
| WO | WO 2018/093971 | 5/2018 |
| WO | 2018/116393 | 6/2018 |

OTHER PUBLICATIONS

Ogorodnikova, Robot introduction in Human work environment. Developments, Challenges and Solutions, 2007, IEEE, p. 167-172 (Year: 2007).*

Baerveldt, Cooperation between man and robot: interface and safety, 2002, IEEE, p. 183-187 (Year: 2002).*

Fahn et al., Real-time face tracking techniques used for the interaction between humans and robots, 2010, IEEE, pg. (Year: 2010).*

* cited by examiner

DETACHABLE END EFFECTORS FOR COSMETICS ROBOTICS

CROSS-REFERENCE TO RELATED APPLICATIONS

This application represents the U.S. National Phase of International Application number PCT/US2019/051496, filed on Sep. 17, 2019 and titled "Detachable End Effectors for Cosmetic Robotics" which claims the benefit of U.S. Provisional Application No. 62/750,582, which was filed on Oct. 25, 2018 and titled "Detachable End Effectors for Cosmetics Robotics". The entire contents of these applications are incorporated herein by reference.

FIELD OF THE INVENTION

The invention relates to the process of automatically applying eyelash extensions.

BACKGROUND OF THE INVENTION

Eyelash extensions are increasing in popularity all over the world. Eyelash extensions are usually differentiated from what is called an "artificial eyelash" or an "artificial eyelash structure" by the fact that they are affixed one to one to a natural eyelash fiber. An "artificial eyelash" is a complete set of eyelash fibers (usually for one eye) that is connected to a backing material (a thin strip at the proximal end of the eyelash fibers), which is affixed to the eyelid. This process is therefore simpler and is provided for home use. Eyelash extensions, however, are laboriously glued, usually with a cyanoacrylate adhesive, to each natural eyelash fiber one at a time by a beauty technician. Extensions may have branches, such as shown in U.S. Pat. No. 8,127,774, and there are some schemes for interlocking with nearby eyelashes, such as disclosed in U.S. Pat. No. 8,113,218.

When eyelash extensions are applied for the first time, the appointment can take a considerable amount of time, lasting up to two hours. During an appointment, each eyelash extension must be picked up in the proper orientation with tweezers, dipped in adhesive, and then placed against one of the subject's natural eyelash fibers until adhesion occurs. Because this large amount of labor costs beauty salons money, and because the length of time required and cost deters some customers, there have been some labor-saving devices proposed. One such device is a dispenser for eyelashes that is held in the hand, disclosed in U.S. Patent Application Publication No. 2014/0261514. There have also been labor saving proposals regarding the trays on which the extensions come from the factory, such as can be seen in U.S. Pat. No. 8,701,685. These trays are intended to combat the fact that it is not only the adhesion step of the process which is difficult for humans. Just picking the eyelash extensions up with a pair of tweezers is challenging. Also, it has been proposed that the handling of adhesive and the step of dipping the extension into adhesive can be eliminated by providing each extension with a pre-installed piece of heat shrink tubing which is used to affix the extension to the natural eyelash fiber. The invention described here applies to all eyelash extensions, whether branched, interlocked, or otherwise, and to all methods of adhesion to the natural eyelash, whether by adhesive, heat shrink tubing, or otherwise.

There is a need, therefore, for a way to more effectively install eyelash extensions, which would reduce both the time and the cost of doing so. Furthermore, there is a need that such a system should be demonstrably safe so that the recipient of the extensions is confident in the procedure. It is very difficult to create a robotic system which is in contact with a human but can be guaranteed to be safe. The robotic system disclosed here provides such safety but does it in a way that is much lower cost than what is normally called "intrinsically safe" or "collaborative" robotics. Safety is typically guaranteed on such systems through the use of redundant feedback (to eliminate axis runaways when a feedback device fails) and through extensive code review coupled with verification and validation testing of all software used on the system. Examples of such systems are the da Vinci® robot of Intuitive Surgical® Corporation of Sunnyvale, Calif. and the ARTAS® robot of Restoration Robotics™, Inc. of San Jose, Calif.

The ARTAS® robot, for example, is based on a version of an industrial robot arm which is expensive, but rated safe for human-robot collaboration. Furthermore, all software which could result in an unsafe situation to the nearby human needs to be meticulously reviewed and tested. This unfortunately raises costs again and cuts the programming staff off from reusing most commercial and open source software libraries and tools. It is hard to guarantee the safety of such software, and, for medical devices, it is considered "Software of Unknown Provenance" by regulating bodies such as the U.S. FDA and is almost impossible to use in any application affecting human safety.

The invention described here addresses this issue by using a novel strategy to make a robot which is in contact with a human safe. It is applicable not only to the job of eyelash extensions but also to other procedures performed on a human subject that could be done by a robot.

SUMMARY OF THE INVENTION

The installation of eyelash extensions can be automated with robotic mechanisms that place the extension without requiring manual application by a human. Unless, however, extremely expensive and complex fail-safe robotic mechanisms and software are used, a safety system should be provided to ensure the safety of the extension process in the event of a robotic malfunction. The subject of this invention is the combined use of inherently safe end effectors, release mechanisms with which they are mounted, and safety barriers attached to robotic mechanisms. A particular method of mounting an end effector that can grasp eyelash extensions and operate near a human face without risk of injuring the human if the end effector contacts the human is also disclosed. This invention also applies to other areas of cosmetics, and embodiments relating to inherently safe operation in tattooing, among others, are presented.

Additional objects, features and advantages of the invention will become more readily apparent from the following detailed description of preferred embodiments thereof when taken in conjunction with the drawings wherein like reference numerals refer to common parts in the several views.

DETAILED DESCRIPTION OF THE INVENTION

There are several embodiments of the invention. Discussion will begin with background for comparison and a rather simple embodiment for eyelash extension. Next, various improvements to the eyelash extension end effector will be discussed. Then, several embodiments using the same basic safety system for other cosmetic applications will be presented. Finally, an exemplary embodiment for use with eyelash extension is given.

The following description sets forth numerous specific configurations, parameters, and the like. It should be recognized, however, that such description is not intended as a limitation on the scope of the present invention but is instead provided as a description of exemplary embodiments.

In the following description, when the term "eyelash" is used, it is meant to refer to one or more natural eyelash fibers of a person. When the term "eyelash extension" or "extension" is used, it is meant to refer to an artificial eyelash extension.

Background and Simplest Embodiment

Figure 1:
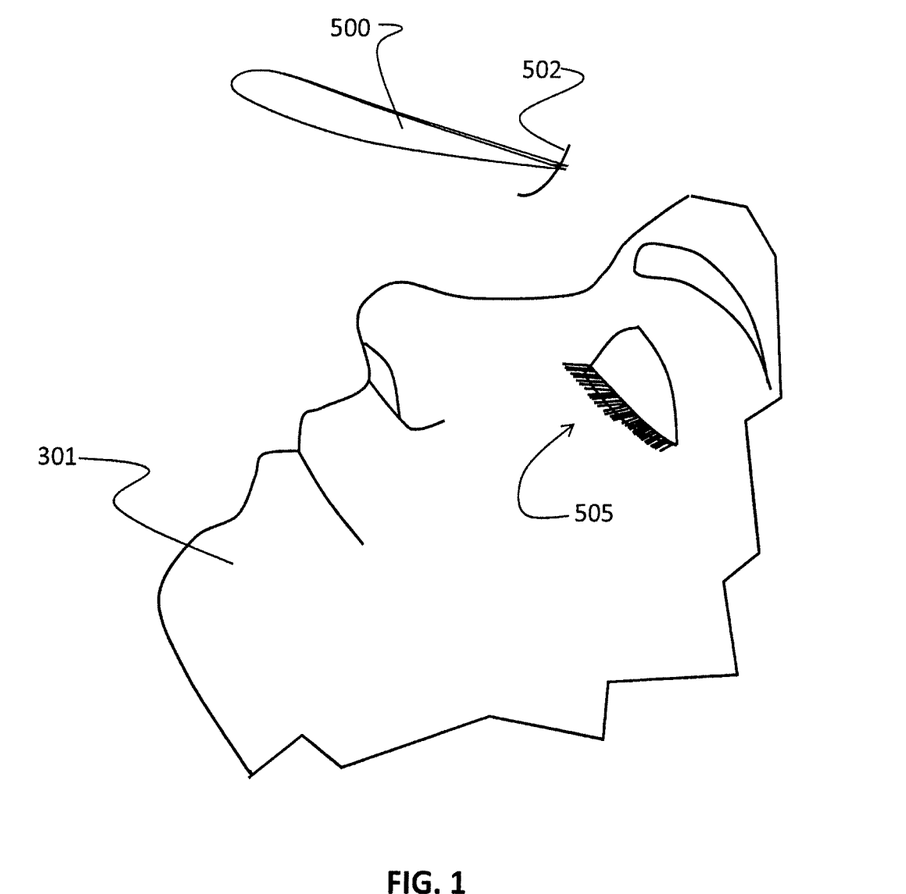
FIG. 1 shows manual eyelash extension.

Consider initially FIG. 1, which is a rather simple figure indicating the present method of eyelash extension. In this process, a cosmetologist (not shown) uses tweezers 500 to manipulate an eyelash extension 502. After applying adhesive to eyelash extension 502, the cosmetologist aligns eyelash extension 502 to a natural eyelash of eyelashes 505 of a subject 301 and waits until the adhesive cures. Safety in this operation is assured by the training of the cosmetologist who has spent many hours learning to apply extensions to purpose-made mannequins. Yet, the hazards associated with operating tweezers 500 in close proximity to the eye of subject 301 are obvious: even a slight grazing of the eye with the razor-sharp tweezers used in eyelash extension could cause serious injury.

Advances in robotics and computer vision have now made it possible to contemplate automating eyelash extension. Although not specifically the object of this invention, a brief recitation of the principal features of such a system will be helpful, and a system is diagrammed in FIG. 2 and set forth in more detail in WO 2018/093971 which is incorporated herein by reference. Here, a robot 530 is comprised of six actuators roughly approximating a human arm. Such configurations are common in the field of robotics and are often referred to as six-axis robot arms. Robot 530 terminates in a tweezer mount 531 which mounts and actuates tweezers 500 to robot 530. In this design, tweezers 500 are simply the same as would be used by a cosmetologist. Tweezers 500 grasp eyelash extension 502, and robot 530 aligns eyelash extension 502 alongside a single eyelash of eyelashes 505. A computer vision system 504 provides an accurate position of eyelashes 505.

Figure 2:
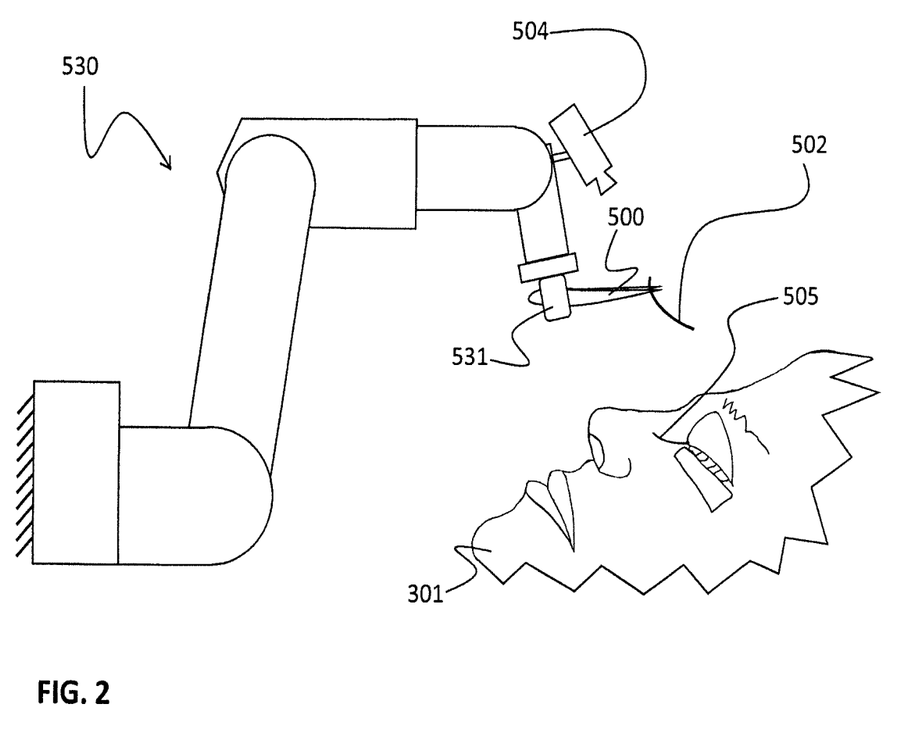
FIG. 2 shows a six-axis robot performing automatic eyelash extension.

Providing safety for this design involves ensuring that robot 530 does not accidentally push tweezers 500 into the head—and especially not into the eye—of subject 301. Such robots exist. For example, surgical robots have become increasingly common in recent years and are used with sharp surgical tools inside patients. Yet, there are several difficulties with such a design. First, great redundancy should be built into the hardware systems; typically, redundancy in sensing and computing are provided at a minimum. This adds cost and complexity to the robot. Second, greater care should be taken with the software; the processes to produce safety critical software are well understood but take great amounts of time, greatly increasing development costs. Thirdly, many such systems are operated directly by a human and do no operate autonomously, adding a layer of safety because the human operator can check the behavior of the robot. Finally, such processes generally preclude more sophisticated computing techniques such as machine learning and artificial intelligence—exactly the types of sophisticated techniques often used with computer vision. This is because it can be difficult to prove that such techniques work correctly and will continue to work correctly under all circumstances.

For these reasons, it would be desirable if there was a way to use a cheaper, more conventional robot to perform light cosmetics-type work without sacrificing safety. That is, can an intrinsically safe robot be designed that does not incur these additional difficulties? After all, there exist a great many relatively cheap, small robots built for industrial applications that can perform tasks such as eyelash extension, but the limitation in their application is the desire for sufficient safety for use around a human. The invention disclosed herein is a device that solves this problem for the small and light payloads needed in cosmetic applications. Of course, it should be noted that there are many approaches to safety that may be used, either singly or in conjunction with the embodiments disclosed here, to provide the required level of safety to the subject.

Figure 3:
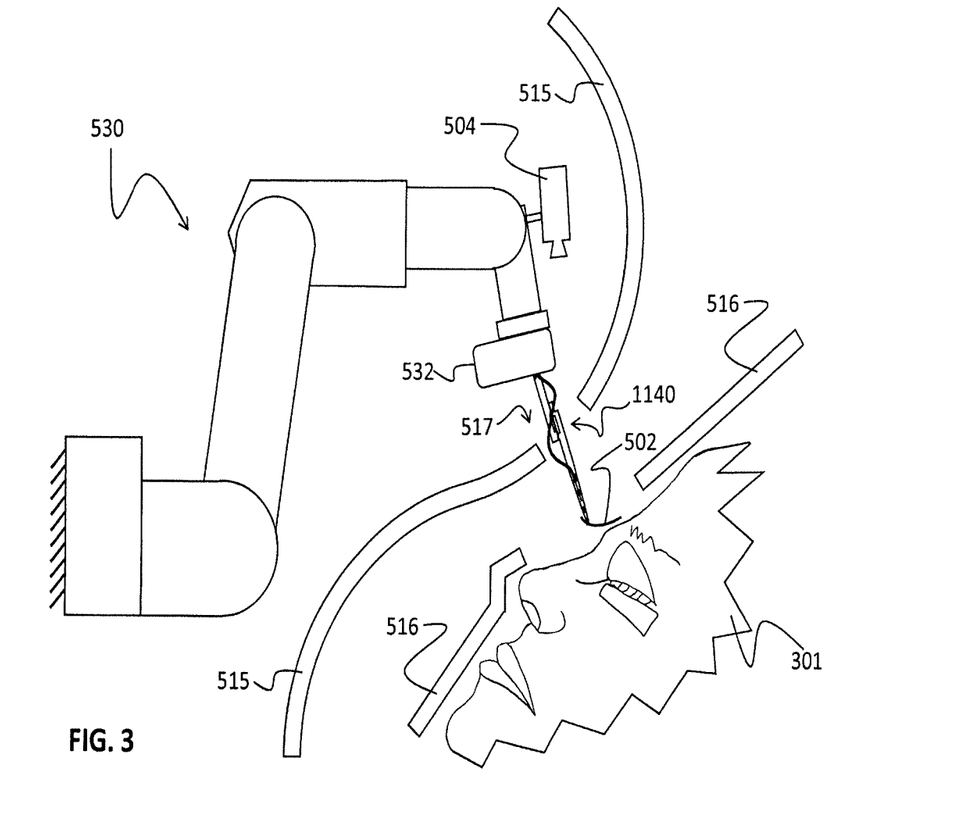
FIG. 3 shows the end effector in use with the robot.

An embodiment of the invention is shown in FIG. 3. Here, robot 530 has been fitted with end effector 1140. End effector 1140 protrudes though a physical barrier 515 at a gap 517, but robot flange 532 cannot fit through gap 517. A second barrier 516, controls how close the face of subject 301 can approach barrier 515 and gap 517. Physical barrier 515 is a first example of a safety barrier and can be made from any material sufficiently strong to resist the maximal impact of robot 530—metals and high impact plastics like polycarbonate are very suitable. End effector 1140 is configured with a release connector or mechanism. The release mechanism is configured such that if a significant load is put on end effector 1140 (such as in the case of an unintended collision with the subject 301), the structural connection between the tip of end effector 1140 and robot 530 is released. This protects subject 301 from any significant force between themselves and end effector 1140. Some of these components can be omitted in specific embodiments, but, in general, it is possible to retrofit a robot to become intrinsically safe with the proper end effector and barriers.

Figure 4:
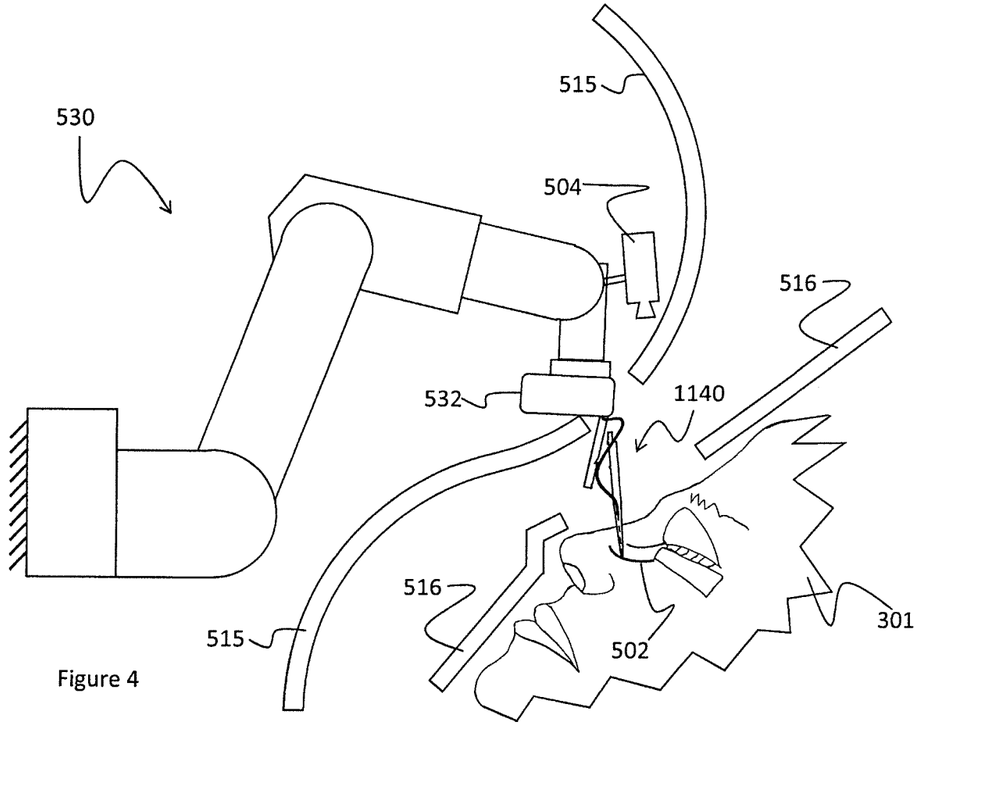
FIG. 4 shows a runaway condition where the robot has malfunctioned, but the subject remains safe due to the use of the end effector.

FIG. 4 shows the outcome of a situation where robot 530 has inadvertently contacted subject 301 with end effector 1140 at a contact point 520. Although good practice in robotic design should limit such an occurrence, it is well understood in the art that, in the absence of the extreme precautions taken in, for example, robotic surgery devices, end effector 506 might contact subject 301 at some point. However, because end effector 1140 includes a release mechanism, the tip of end effector 1140 simply detaches. Furthermore, robot 530 has contacted physical barrier 515, which prevents further motion, and the upstream portion of end effector 1140 (that portion still connected to the robot) cannot reach the subject 301's face which is contained by the second barrier 516. Therefore, the embodiment of FIG. 4 shows an inherently safe robotic system for use adjacent to a human subject where the safety is provided by mechanical means.

In some embodiments, a breakaway connection is provided as part of the end effector. This may be advantageous for several reasons: so that the maximum force produced upon a collision with the end effector may be accurately controlled; so that the force generated at breakaway may be highly directional; so that the end effector need not be deformable under low loads; so that sharp ends are not generated by a breaking end effector; and so that, as an ancillary benefit, the distal portion of the end effector may be swapped (e.g., for sanitary reasons).

Figures 5A, 5B, 5C:
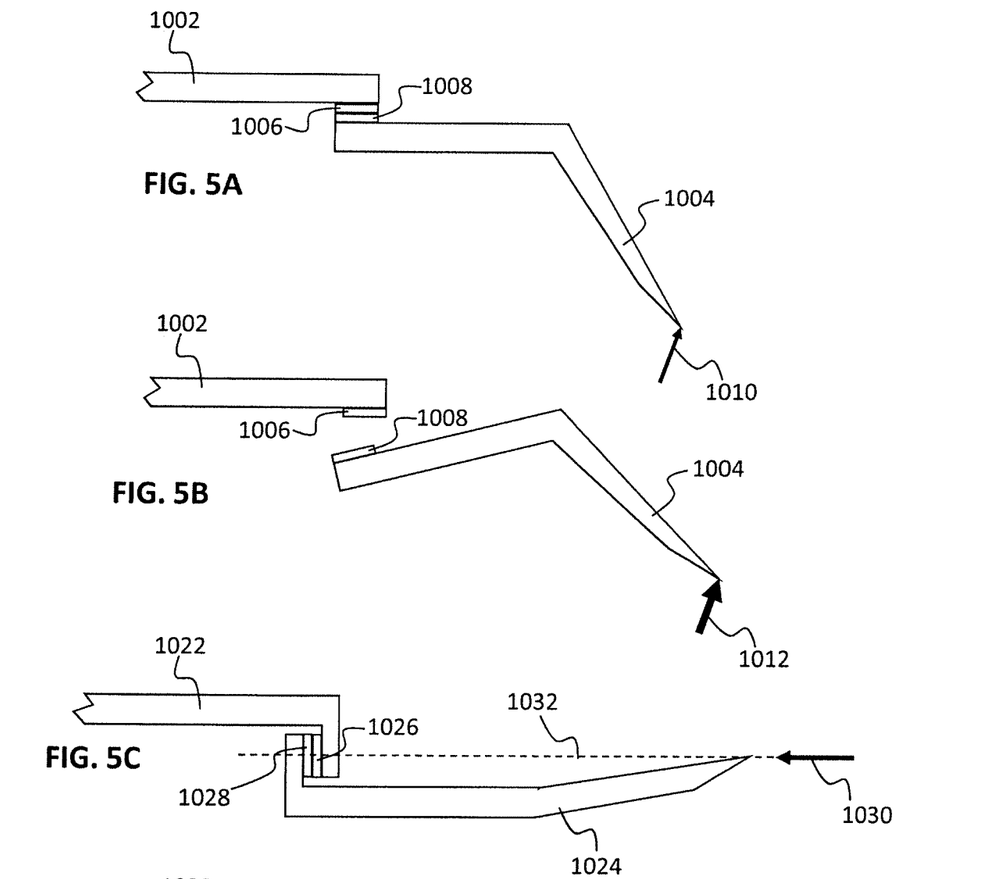
FIG. 5A shows a simple break away end effector.
FIG. 5B shows the end effector of FIG. 5A in the broken away condition.
FIG. 5C shows an alternate geometry of a simple break away end effector.

Consider, initially, a rather simple embodiment of an end effector containing a break away or release mechanism that is shown mated in FIG. 5A. Here the end effector shown is one half of a pair of end effectors used to isolate an eyelash, although the invention is not limited to this application. The end effector is comprised of proximal portion 1002 and distal portion 1004, and proximal magnet 1006 affixed to proximal portion 1002, and distal magnet 1008 affixed to distal portion 1004. Proximal magnet 1006 and distal magnet 1008 are arranged such that they attract one another. For example, this could be achieved by having the north pole of proximal magnet 1006 on its lower side, and the south pole of distal magnet 1008 on its upper side, but there are many similar arrangements, including for magnets with many poles, that will similarly attract the two magnets to one another. The magnets here are affixed with adhesive (not shown) but could just as well be affixed with mechanical fasteners, a press fit, or any of many ways known to the art to securely affix a magnet to another surface.

Under the presence of low interaction load 1010, distal magnet 1008 and proximal magnet 1006 remain in contact, unmoving. In FIG. 5B, high interaction load 1012 has caused distal magnet 1008 to peel away from proximal magnet 1006, leading distal portion 1004 to no longer be connected to proximal portion 1002. In the embodiment where proximal portion 1002 is connected to a robotic system, and distal portion 1004 is an end effector or connected to an end effector, this action may be used as one element to ensure safety, as well as a way to replace distal portion 1004 to maintain hygiene. By ensuring that high interaction load 1012 is greater than any working load that should be experienced in operation, and that high interaction load 1012 is lower than any load that might damage or injure the object of the end effector, the safety and integrity of the object manipulated by the end effector may be assured if (through the use of properly designed safety barriers) it is insured that proximal portion 1002 cannot touch subject 301.

It is a property of this design that the critical load at which the end effector breaks away (or releases) is dependent not only on the strength of magnets used (and there are a great many options in this design space alone) but also on the geometric relationship between the point of interaction of load and the magnetic coupling; it will also depend on the geometry of the magnets; it will also depend on the coefficient of friction between the magnets and any other surfaces in contact between the proximal and distal portions 1002 and 1004. This provides a great deal of freedom to the designer to choose not only the magnitude of the critical load at which the end effector breaks away, but also that magnitude as a function of the angle of application of the load. That is, the end effector may be designed to preferentially break away under some directions of load more than others. Exact analytical solutions, while possible, are of somewhat limited use because variability in coefficients of friction may change which mode of motion occurs first during breakaway (e.g., a sliding versus a peeling separation of the magnets). We have found that in practice, it is most useful to perform empirical characterization and design iteration to achieve the desired breakaway characteristics.

While there is a preference for high force density magnets such as "rare earth" magnets (e.g., neodymium magnets), various other types of magnets such as, without exclusion, ferrite and Alnico are also suitable. In some embodiments other means of connecting the proximal and distal portions may be used, such as adhesives, double stick tape, and elastic bands.

Figure 5D:
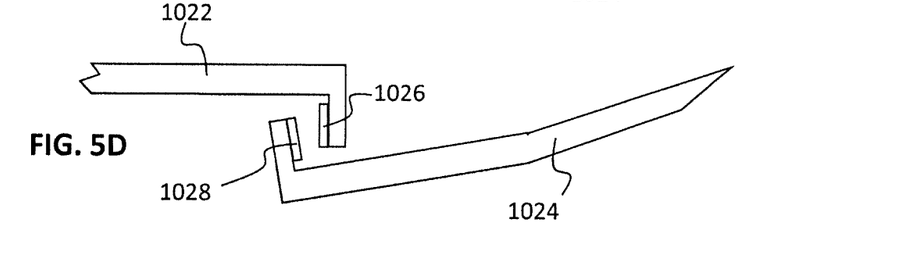
FIG. 5D shows the end effector of FIG. 5C in the broken away condition.

FIGS. 5C and 5D show a variation where the axes of the magnets have been rotated so that they couple vertically rather than horizontally. So doing changes the orientation of the breakaway and therefor may change the mode of separation between proximal and distal magnets 1026 and 1028 respectively (because the orientation of the magnets at the breakaway point have changed with respect to the resultant forces). In this embodiment, distal portion 1024 has a slightly different geometry such that purely compressive forces along dashed line 1032 will generate a pure tension between proximal and distal magnets 1026 and 1028 respectively. It is therefore very simple to design the breakaway mechanism since the level of compressive force 1030 that will induce the breakaway is simply the level of force that will cause proximal and distal magnets 1026 and 1028 to separate. This simplicity of design is an advantage of this embodiment.

It is not necessary for both the proximal and distal segments to have magnets. For example, in FIG. 6A, distal segment 1049 includes magnetic plate 1043, which may be made of any material attracted to a magnet (e.g., iron, nickel and some steels) while proximal segment 1040 includes magnet 1042. Of course, the attractive force will be different between a magnet and a magnetic material rather than between two magnets, but this simply provides the designer a further flexibility in the design. Of course, the magnet and the magnetic material may be placed in either proximal or distal links; here the choice to put the magnetic material in the distal link is driven by a desire to reduce the manufacturing cost of the distal link which may be single use, and magnetic materials (especially steel) are generally cheaper than magnets.

Figure 6A:
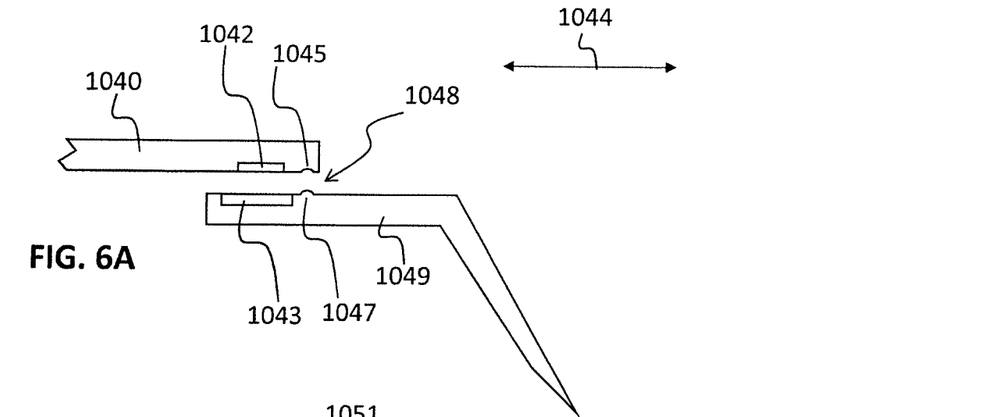
FIG. 6A shows another variation on the end effector with a detent and other details.

Further, both magnet 1042 and magnetic plate 1043 are recessed into the body of proximal segment 1040 and distal segment 1049 and flush to the surfaces. It is also possible to recess either the magnet or magnetic material below the surfaces of their respective segments to create an airgap between the magnet and the magnetic material that greatly reduces the attraction force, providing further control to the designer. Of course, nonmagnetic materials (e.g. most plastics and metals) can fill the air gap resulting in a magnet or magnetic material being completely enclosed within the proximal or distal segments. This may be helpful in making the segments cleanable or easier to manufacture. Distal portion 1049 for example could be an injection molded plastic component molded over a stainless steel plate insert 1043, and the plastic material could encase the majority of the insert 1043. Care must be taken in this case to use a stainless steel that is magnetic.

FIG. 6A also shows detent receiver 1045 and detent protrusion 1047 which mate when magnet 1042 and magnetic plate 1043 are coupled. Detent receiver and protrusion 1045 and 1047 comprise detent 1048. Detent 1048 helps locate distal segment 1049 with respect to proximal segment 1040, which ensures a repeatable geometry between the tip of distal segment 1049 and any robotic system driving proximal link 1040. As shown, detent 1048 extends into the page and inhibits motion along double arrow 1044, but, conversely a different detent could be placed along the direction of double arrow 1044 and inhibit motion into the page. In some embodiments, it may be desirable to inhibit motion along both axes, using two or more detents. In some embodiments, this may be achieved by two point detents rather than detents that run the width or length of the segments; the detents may even be more complex keying features that control the orientation very exactly. However, it is important to note that detents can also increase the forces needed to cause the breakaway to occur, and the designer must be careful to balance these requirements.

Figure 6B:
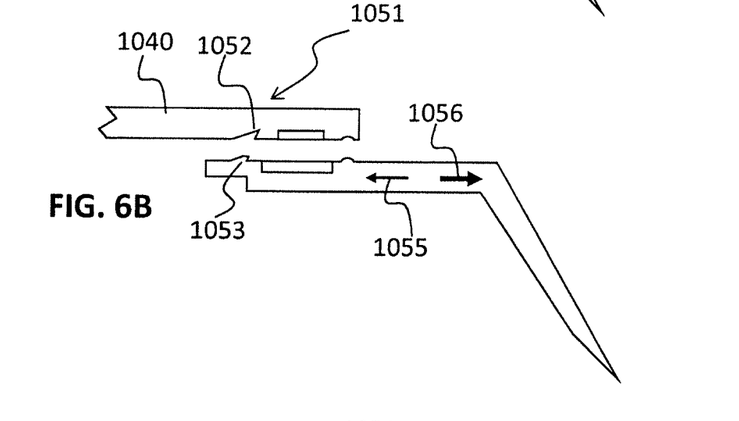
FIG. 6B shows another variation on the end effector with a directional detent and other details.

FIG. 6B shows an embodiment further including directional detent 1051 comprised of directional detent receiver 1052 and directional detent protrusion 1053. Because directional detent protrusion 1053 will "catch" when pulled to the right and not to the left, rightward disengaging force 1056 may be larger than leftward disengaging force 1055. This is helpful in the case that the end effector needs to be able to pull with more force than push. In the particular art of robotic eyelash extension, this is helpful in order to pull eyelash extensions from a supply (where they are often taped to a substrate) without increasing the compressive force at which breakaway occurs.

Figure 6C:
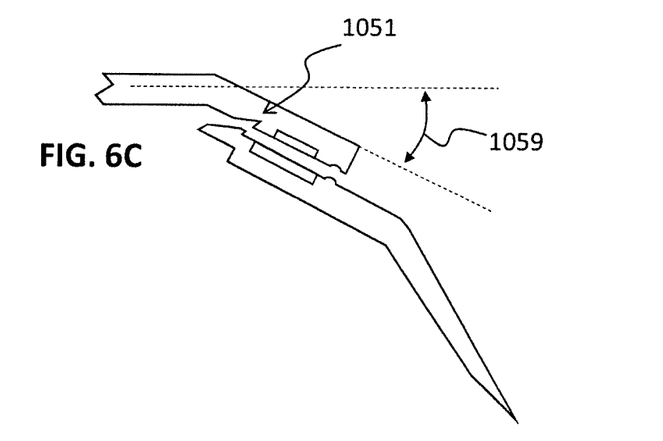
FIG. 6C shows an alternate version of the end effector of FIG. 6B.

FIG. 6C shows another embodiment where the breakaway mechanism of the previous embodiments has been rotated by angle 1059, changing the relationship between direction detent 1051 and any forces applied to the end effector.

This invention is of particular utility in embodiments where a computer vision (sometimes referred to as machine vision) system is used. Consider FIG. 7, where cameras 1153 and 1154 are in communication with computer 1160, together comprising stereoscopic computer vision system 1161. Distal segment 1049 includes fiducial marker tang 1150, upon which is mounted fiducial marker 1152. Robotic system 1058 is coupled to both proximal segment 1040 and cameras 1153 and 1154, through various actuators and structural elements which are not shown. Despite the use of a detent in the design of the end effector, the orientation of distal segment 1049 will have some uncertainty. When fiducial marker 1152 is visible to cameras 1153 and 1154, computer vision system 1161 will be able to correct for errors in the orientation of distal segment 1049 and will therefore be able to estimate the position of distal segment tip 1163 with greater accuracy. In some embodiments, where distal segment tip 1163 is highly visible and easy to recognize, computer vision system 1161 may be able to measure the position of tip 1163 directly, obviating the need for fiducial marker 1150 and associated fiducial marker tang 1150. In some embodiments, multiple fiducials may be used to provide enhanced positional and orientational resolution. In some embodiments, components of distal segment 1049 may be used as fiducial markers directly. In some embodiment, especially where direct measurement of the position of tip 1163 is possible, other types of computer vision system are possible, such as laser range finders, LiDAR scanners, and various structured light sensors.

Figure 7:
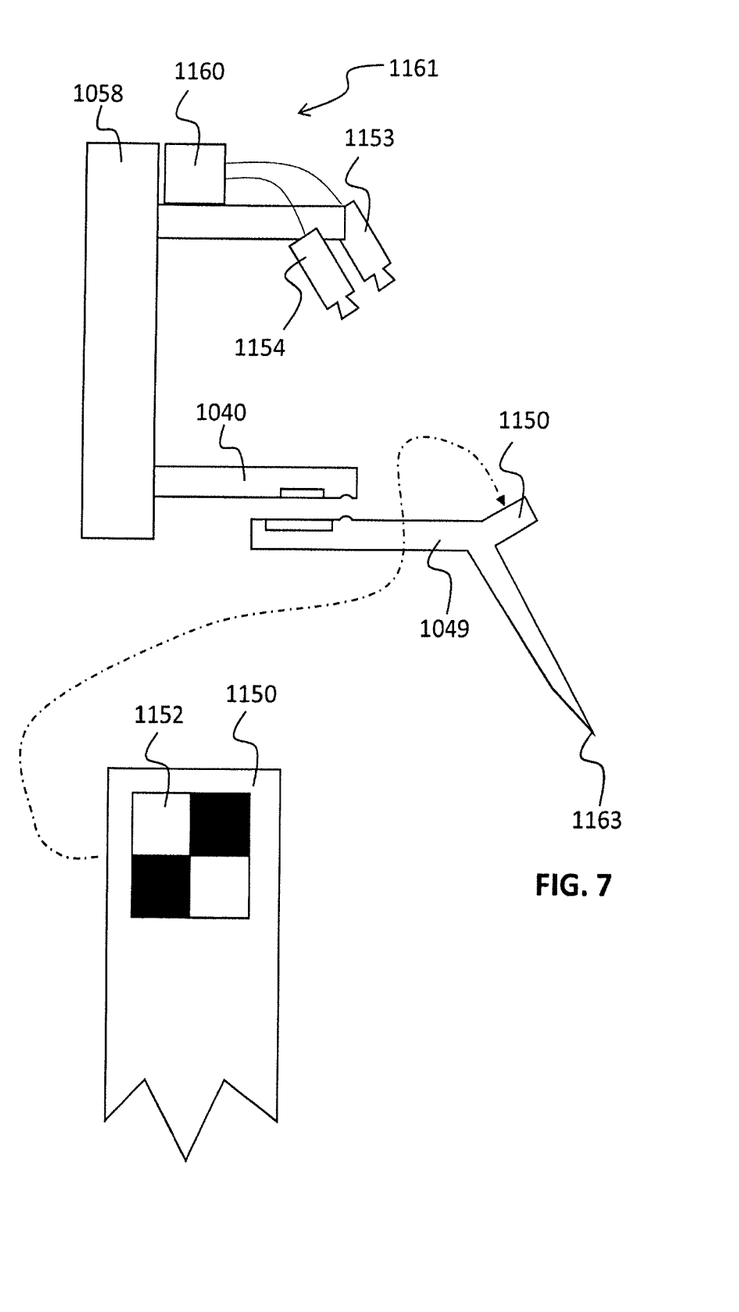
FIG. 7 shows an end effector being used in concert with a computer vision system.

The embodiment shown in FIG. 7 is important because it may not be practical to provide sufficient keying features to exactly align distal and proximal segments 1049 and 1040 because, as discussed above, providing such features may unacceptably increase the breakaway forces. Because the breakaway interface between distal and proximal segments 1049 and 1040 involves two surfaces pressed together, it tends to exhibit static friction (sometimes referred to as "stiction"). This means that the distal and proximal segments 1049 and 1040 will not move with respect to one another below a slip force that is close to the force required to separate the segments when they break away. Therefore, below this slip force, the distal and proximal segments 1049 and 1040 act as a single unit; as long as this slip force is not exceeded, the geometric relationship between them is preserved. As a result, the computer vision system need only measure the orientation of distal segment tip 1163 once, not continuously, in order to accurately understand its position in space. This is particularly useful when working with a robotic system where distal segment tip 1163 may be selectively positioned in front of a blank background to allow for measurement of its orientation by computer vision system 1160 without fiducial 1152. Once this measurement is taken and the relationship between distal segment tip 1163 and the robotic system is known, the end effector may be reoriented and the position of distal segment tip 1163 known without requiring further measurements. In some embodiments, the robotic system may have some knowledge of position of distal segment tip 1163 in the form of a model of itself based on known geometric parameters and various sensors, in which case the measurement may simply be used to refine the model.

Figure 8:
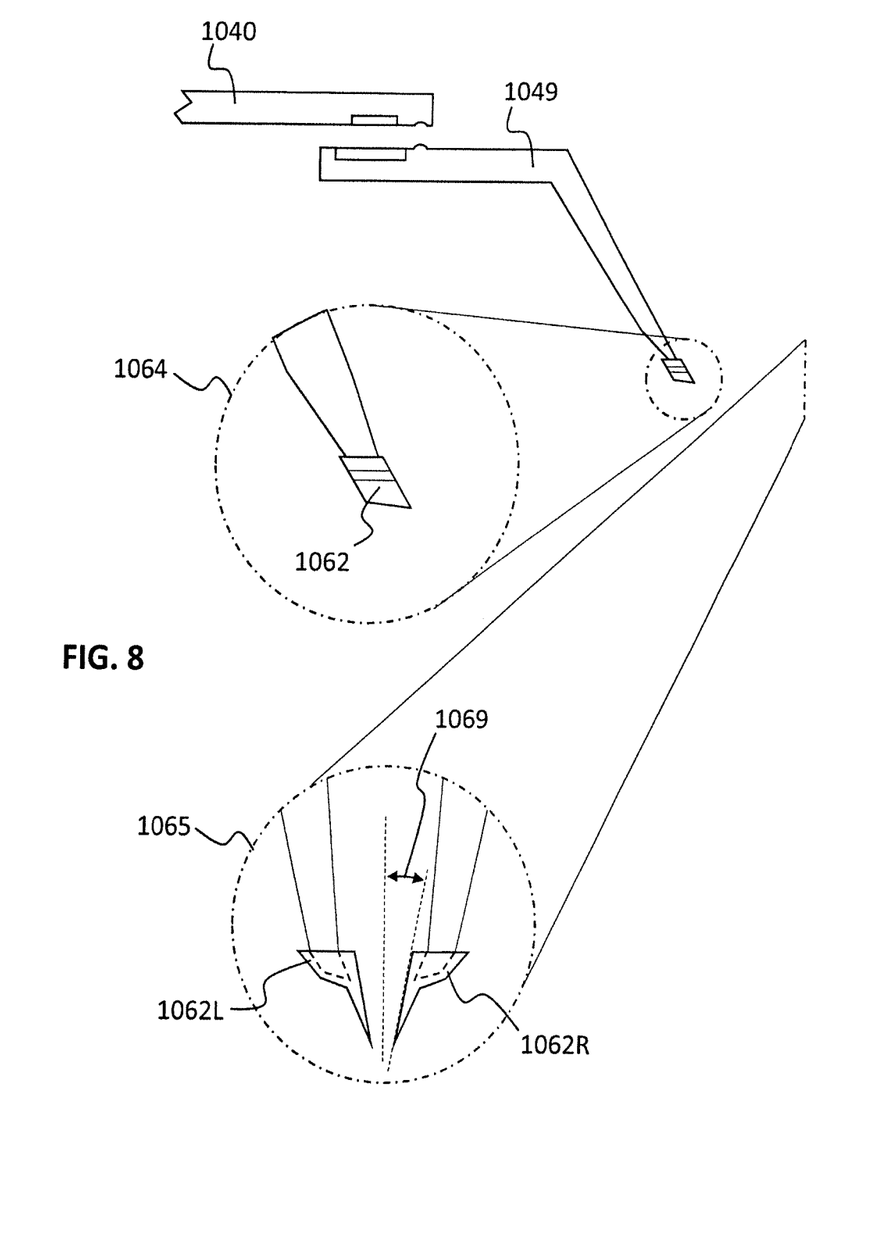
FIG. 8 shows a novel tip for a version of the end effector used to isolate natural human eyelashes.

FIG. 8 shows an embodiment of distal segment 1049 that is particularly useful in the application of separating and isolation individual eyelashes. Detailed view 1064 shows a side view of isolation tip 1062, which is made of a rubber or other compliant material. In the even that distal segment 1049 touches a person, isolation tip 1062 will deform and then the breakaway connection to proximal segment 1040 will breakaway. Front view 1065 shows both left and right isolation tips (1062L and 1062R respectively) that are used to isolate a single eyelash. For the isolation to be effective, the isolations tips must meet at their very tips, and so angle 1069 must be greater than or equal to zero. In embodiments where the isolation tips do not have flat sides, it is sufficient to require that the distal most point of the tips are the first part of the tips to contact as the pair of tips is closed.

Figure 9A:
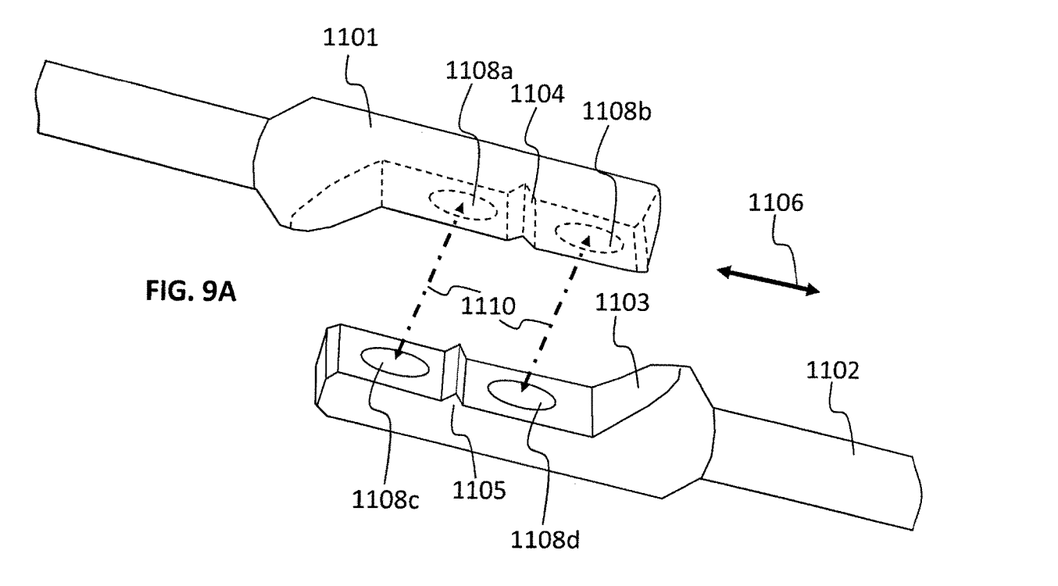
FIG. 9A depicts another embodiment of an end effector break away joint with a different configuration.
Figure 9B:
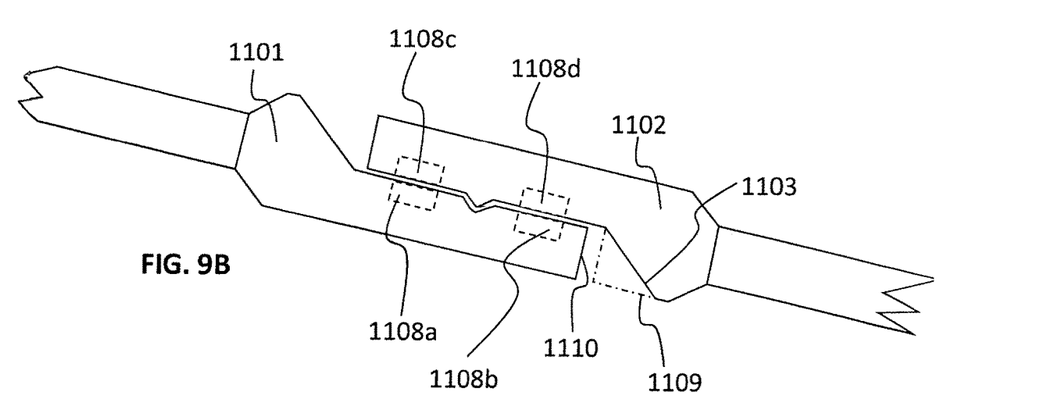
FIG. 9B depicts a side view of the assembled version of the end effector of FIG. 9A.

FIG. 9A shows a perspective drawing of a particular breakaway connection embodiment, and FIG. 9B shows a side view of the same. Here the proximal connection to the robot and distal connection to the remainder of the end effector are cut away. Proximal segment 1101 and distal segment 1102 are identical except for the gender of detent 1105; therefore, there is nothing particular about their designation as proximal and distal as long as each pair has appropriately mating detents. Four magnets, 1108*a-d*, are arranged in two pairs holding the breakaway connection together, and mating as shown by arrows 1110. Further included in this embodiment is ramp 1103 which facilitates disengagement under compressive loads along the direction of double arrow 1106. If ramp 1103 were instead a vertical feature, as indicated in FIG. 9B as vertical end 1109, then butt end 1110 of proximal segment 1101 would collide with vertical end 1109 and could accept very high compressive loads in the direction of double arrow 1106. This is undesirable in many conditions as it would greatly increase the effective breakaway loads.

The breakaway connection is useful with end effectors that are more complex than simply the eyelash isolation end effectors discussed so far. In some embodiments, they may be used with grippers where the actuation of the gripper is provided through a flexible connection or transmission so that the breakaway connection is not held together by the actuation transmission. Such a flexible connection may be provided by transmitting power to the gripper through a fluid power connection, such as pneumatic or hydraulic, or through a mechanical transmission such as a Bowden cable or flexible shaft. Of course, electrical transmission of power past the breakaway is possible, but having an electric motor on the distal segment increases its mass, increasing the likelihood that high accelerations—common in time conscious robotics applications—may accidentally decouple the breakaway.

Figure 10A:
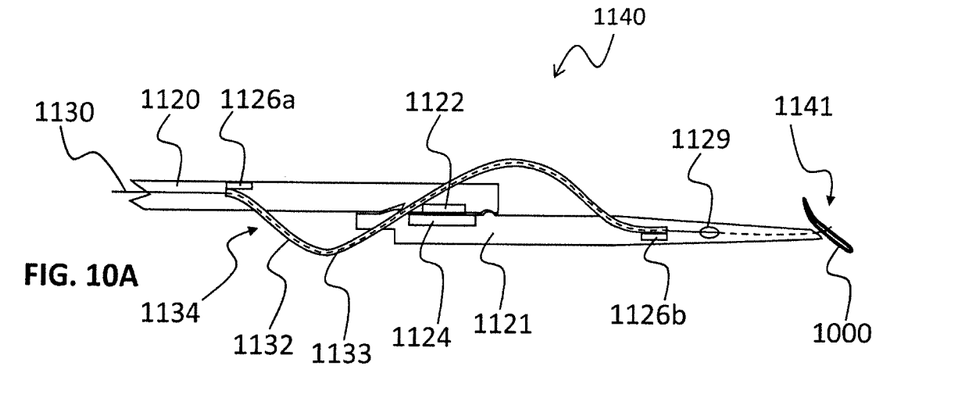
FIG. 10A shows an eyelash extension handling end effector which incorporates a break away joint.
Figure 10B:
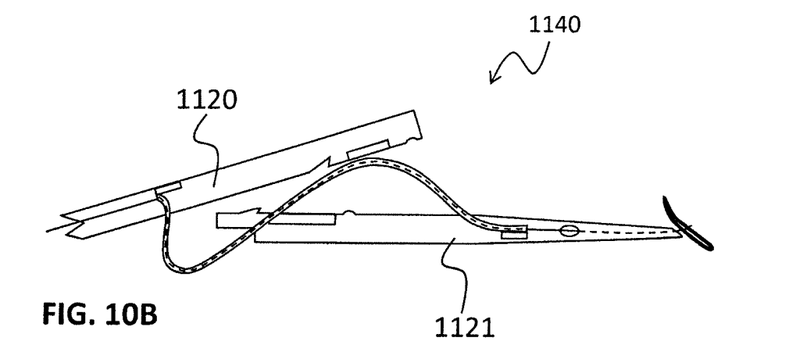
FIG. 10B shows the eyelash extension handling end effector of FIG. 10A in the broken away state.

FIG. 10A shows end effector 1140 that is designed for manipulation of an eyelash extension using cord gripper 1141 (such as those disclosed in International Patent Application PCT/US2017/061899) and Bowden cable 1134. Bowden cable 1134 is comprised of sheath 1132 and cable 1133. In this embodiment, cable 1133 connects to the loop of cord gripper 1141 near the tip of distal segment 1121 in a connection not visible but located near exit point 1129 of cable 1133. Sheath 1132 is flexible and coupled to proximal segment 1120 with ferrule 1126*a* and to distal segment 1121 with ferrule 1126*b*. Cable 1130, which is simply an extension of cable 1133 extends to the robotic system, not shown, where it may be pulled by an actuator such as an electric motor. The detents, proximal magnet 1122, and distal magnetic plate 1124 are the same as the embodiment of FIG. 6B. When cable 1130 is pulled by the robotic system, cord gripper 1141 closes around extension 1000; when cable 1130 is (gently) pushed by the robotic system, cord gripper 1141 releases extension 1000. Because compressive loads are carried by sheath 1132 and balanced by cable 1133, no load is generated at the breakaway by actuation forces transmitted through Bowden cable 1134. FIG. 10B simply shows the end effector 1140 with the breakaway disconnected.

Figure 11A:
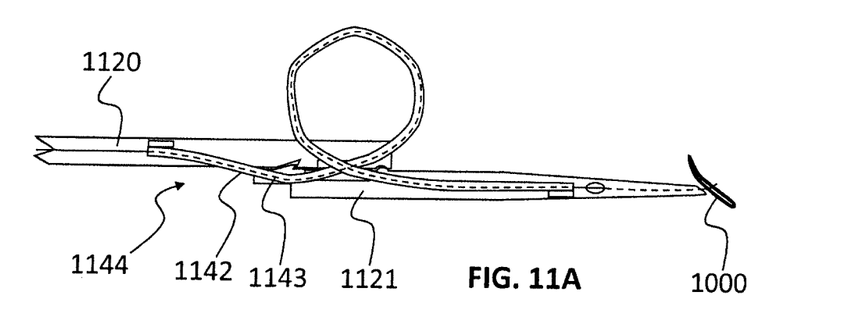
FIG. 11A shows an alternate routing of the Bowden cable shown in FIGS. 10A and 10B.
Figure 11B:
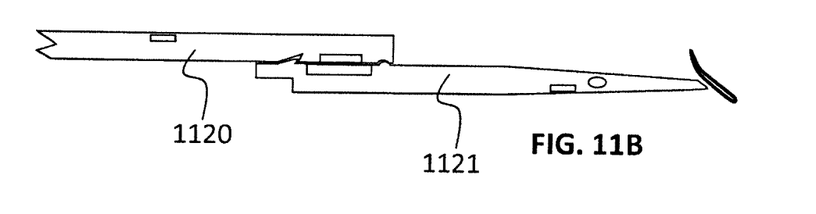
FIG. 11B shows the underlying breakaway end effector structure of FIG. 11A depicted separately for clarity.
Figure 11C:
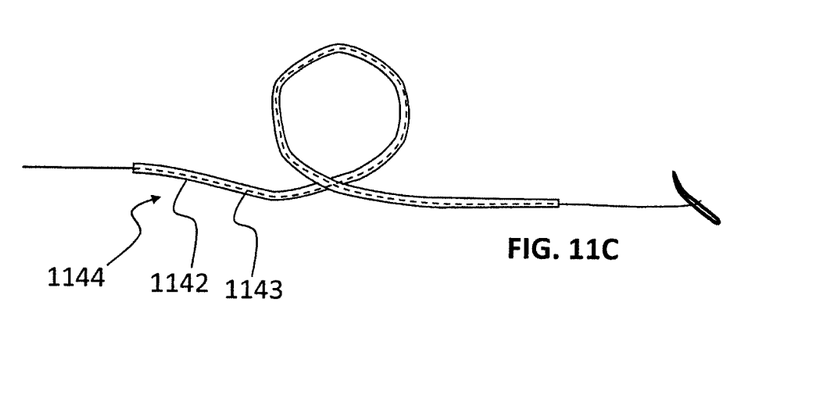
FIG. 11C shows the Bowden cable 1144 of FIG. 11A depicted separately for clarity.

FIG. 11 shows the same end effector as FIG. 10, but with Bowden cable 1144 executing a full loop rather than an "S" shaped bend. FIG. 7A shows the full assembly, with the underlying breakaway end effector structure and Bowden cable 1144 depicted separately for clarity in FIGS. 11B and 11C respectively. The bends in the Bowden cables are necessary to provide slack so that the breakaway may occur. In some embodiments, it may be possible to provide straight Bowden cables if so doing does not inhibit required breakaway, especially if high tension loads on the end effector are desired. Although the actuation loads from the Bowden cables in these examples do not generate load at the breakaway, the bends in the sheath do generate load due to any residual stress produced in bending the sheath from straight. Providing a full loop, as shown in FIG. 11, rather than the "S" bend of FIG. 10 creates a bending moment rather than a tension force in the breakaway connection. Either design may work, and it is simply a matter of choosing a design that does not unacceptably alter the behavior of the breakaway and that meets the spatial and geometric requirements of the design. It is also important to note that any of the other power transmission systems noted earlier (especially fluid power and flexible shafts) will generate load in a similar manner.

Although described with reference to preferred embodiments, it should be understood that various changes and/or modification can be made to the invention without departing from the spirit thereof. In particular, although certain preferred breakaway connectors or mechanisms have been disclosed, it should be readily apparent that various connection arrangements could be employed while still accomplishing the goals set forth above.

The invention claimed is:

1. An intrinsically safe robotic system configured to perform a task on a human subject, the system comprising:
   a robot;
   a computer vision system configured for use in controlling the robot
   a first safety barrier around the robot, wherein the first safety barrier is configured to prohibit operation of the robot beyond the first safety barrier;
   a second safety barrier around the human subject, wherein the second safety barrier is configured to prohibit egress of the human subject beyond the second safety barrier or prohibit operation of the robot if the human subject exits the second safety barrier;
   a space between the first and second safety barriers comprising a safety zone;
   at least one end effector attached to the robot, wherein the end effector is configured to extend through the first and second safety barriers and includes a release mechanism configured to readily release from the robot upon contacting the human subject, wherein the safety zone is crossable only by the at least one end effector, thereby prohibiting direct interaction between the human subject and the robot and protecting the human subject from harm.

2. An intrinsically safe robotic system configured to perform a task on a region of a human subject, the system comprising:
   a robot;
   a computer vision system configured for use in controlling the robot
   a safety barrier between the human subject and the robot, wherein the safety barrier is configured to prohibit interaction between the human subject and the robot;
   an allowable load or pressure defined in correspondence with safe loading for the region;
   at least one end effector attached to the robot, wherein the at least one end effector is configured to extend through the safety barrier and detach structurally when loaded to no more than the allowable load or pressure, and the at least one end effector is restricted to the region by the safety barrier.

3. The intrinsically safe robotic system of claim 2, wherein the safety barrier is formed from a strong, impact-resistant material; and the end effector includes a release mechanism configured to readily release from the robot when loaded to no more than the allowable load or pressure, thereby preventing the at least one end effector from harming the human subject.

4. The intrinsically safe robotic system of claim 3, wherein the at least one end effector includes a flexible strut or tube.

5. The intrinsically safe robotic system of claim 3, wherein the at least one end effector includes a flexible transmission interfacing crossing the release mechanism, thereby allowing actuation distal to the release mechanism without inhibiting the release mechanism.

6. The intrinsically safe robotic system of claim 3, wherein the computer vision system is configured to monitor the orientation of a distal portion of the end effector and to communicate this orientation to the robot.

7. The intrinsically safe robotic system of claim 6 wherein the robotic system maintains a geometric model of the robotic system and the robotic system updates the model based on the orientation of the distal portion.

8. The intrinsically safe robotic system of claim 3, wherein the release mechanism includes a proximal portion and a distal portion, the proximal portion fixed to the robotic system, the distal portion fixed to the end effector, and
the proximal and distal portion include mating detent features whereby the proximal and distal portions have a generally fixed spatial relationship when mated.

9. The intrinsically safe robotic system of claim 8, wherein said mating detent features are asymmetric whereby demating in a first direction requires less force than demating in a second direction.

10. The intrinsically safe robotic system of claim 3, wherein the at least one end effector includes a nail polish brush.

11. The intrinsically safe robotic system of claim 3, wherein the at least one end effector includes a tattooing device.

12. The intrinsically safe robotic system of claim 3, wherein the release mechanism includes at least one magnet.

13. The intrinsically safe robotic system of claim 12, wherein said at least one magnet is coupled to another magnet or a piece of magnetic material thereby forming a magnetic pair attracted to each other.

14. The intrinsically safe robotic system of claim 13, wherein one side of said magnetic pair is mounted permanently to the robot and the other side is mounted to an end effector such that if the force between the two elements of the pair is overcome, the end effector is detached structurally from the robot.

15. The intrinsically safe robotic system of claim 2, wherein the safety barrier includes at least one light curtain.

16. A method of performing a cosmetic procedure on a human subject with a robot, an end effector coupled to the robot, a computer vision system, and a safety barrier, the method comprising:
selecting a region of the human subject for the cosmetic procedure;
defining an allowable load or pressure for the region;
orienting the robot and the safety barrier to limit access to the region;
configuring the end effector to detach at no more than the allowable load or pressure; and
performing the procedure, using the computer vision system.

* * * * *